United States Patent
Caso et al.

(10) Patent No.: US 9,366,660 B2
(45) Date of Patent: Jun. 14, 2016

(54) DEVICE FOR ANALYZING THE INTERNAL ATMOSPHERE OF THE CASING OF AN ELECTRONIC ROTATING MACHINE

(75) Inventors: Tammaro Caso, Staranzano (IT); Gianfranco Zocco, Trieste (IT)

(73) Assignee: Nidec ASI S.p.A., Milan (IT)

( * ) Notice: Subject to any disclaimer, the term of this patent is extended or adjusted under 35 U.S.C. 154(b) by 335 days.

(21) Appl. No.: 14/000,006

(22) PCT Filed: Feb. 15, 2012

(86) PCT No.: PCT/IB2012/050696
§ 371 (c)(1),
(2), (4) Date: Aug. 16, 2013

(87) PCT Pub. No.: WO2012/110965
PCT Pub. Date: Aug. 23, 2012

(65) Prior Publication Data
US 2013/0319083 A1      Dec. 5, 2013

(30) Foreign Application Priority Data
Feb. 16, 2011   (IT) .............................. MI2011A0230

(51) Int. Cl.
*G01N 7/00*      (2006.01)
*G01N 33/22*     (2006.01)
*G01N 33/00*     (2006.01)
*G01N 21/3504*   (2014.01)

(52) U.S. Cl.
CPC ............ *G01N 33/22* (2013.01); *G01N 33/0032* (2013.01); *G01N 33/0063* (2013.01); *G01N 21/3504* (2013.01)

(58) Field of Classification Search
CPC .............. G01N 33/22; G01N 33/0063; G01N 33/0032; G01N 21/3504
See application file for complete search history.

(56) References Cited

U.S. PATENT DOCUMENTS

| | | | |
|---|---|---|---|
| 3,973,848 A | 8/1976 | Jowett et al. | |
| 4,069,018 A | 1/1978 | Karna et al. | |
| 2003/0071629 A1 | 4/2003 | Yang et al. | |

FOREIGN PATENT DOCUMENTS

| | | |
|---|---|---|
| CN | 200972475 Y | 11/2007 |
| GB | 1 604 410 | 12/1981 |
| WO | 93/16376 | 8/1993 |
| WO | 2009/112001 A1 | 9/2009 |

*Primary Examiner* — John Fitzgerald
*Assistant Examiner* — Truong Phan
(74) *Attorney, Agent, or Firm* — Alan G. Towner, Esq.; Pietragallo Gordon Alfano Bosick & Raspanti, LLP

(57) ABSTRACT

The present invention relates to a device for analyzing the internal atmosphere of the casing of an electric rotating machine comprising a housing with an atmosphere inlet opening, a suction pump for drawing the atmosphere within the casing of the electric machine, a pump inlet conduit for placing the atmosphere inlet opening in fluid communication with the suction pump, an atmosphere inlet conduit adapted to place the interior of the casing in fluid communication with the atmosphere inlet opening, transducer means adapted to measure the percentage volume of at least one explosive compound present in the atmosphere drawn by the pump and adapted to generate an electric signal proportional to the percentage volume of the explosive compound. The device also comprises comparison means adapted to compare the percentage volume of at least one explosive compound with a predetermined threshold value of percentage volume. The comparison means are also adapted to generate an electric alarm signal when the predetermined threshold value is exceeded.

9 Claims, 2 Drawing Sheets

DEVICE FOR ANALYZING THE INTERNAL ATMOSPHERE OF THE CASING OF AN ELECTRONIC ROTATING MACHINE

The present invention relates to a device for analysing the internal atmosphere of the casing of an electric rotating machine.

Electric rotating machines are widely used in the industry and comprise, for example, synchronous and asynchronous electric motors typically operating in alternating current.

Among the several applications in which such electric machines are used, their use is critical in environments with a risk of explosion, more or less saturated with gases, vapours and potentially explosive mixtures thereof, such as for example refineries, treatment plants of oil materials, but also chemical and treatment plants of flammable materials. It is therefore possible that such gases and vapours penetrate within the casing of the same electric machine.

The presence of a potentially explosive atmosphere within the casing of the electric machine is a serious risk factor, especially during the start-up step of the same machine, that is, when the machine switches from a de-energised status to an energised status. In this step, in fact, there is a high probability of triggering electric arcs and sparks in the rotating movement of the rotor relative to the stator.

As a consequence, any potentially explosive atmosphere present within the casing of the electric machine may blow up, during the start up step, with consequent damage to the same machine and interruption of the operating cycle of the utilities connected thereto. Moreover, a possible explosion could seriously impair the safety of the operators working in such environments.

From the above description there is clearly the need to check the presence of explosive atmosphere within the casing of an electric rotating machine in order to prevent any damage to the machine and to the operators present in the immediate vicinity of the same.

The object of the present invention is to provide a device for analysing the internal atmosphere of the casing of an electric rotating machine having such structural and functional features as to meet the above needs while obviating the drawbacks mentioned above with reference to the prior art.

Such object is achieved by a device for analysing the internal atmosphere of the casing of an electric rotating machine according to claim 1.

Further features and advantages of the device for analysing the internal atmosphere of the casing of an electric rotating machine according to the present invention will appear more clearly from the following description of a preferred embodiment thereof, given by way of a non-limiting example with reference to the annexed figures, wherein.

Figure 1:
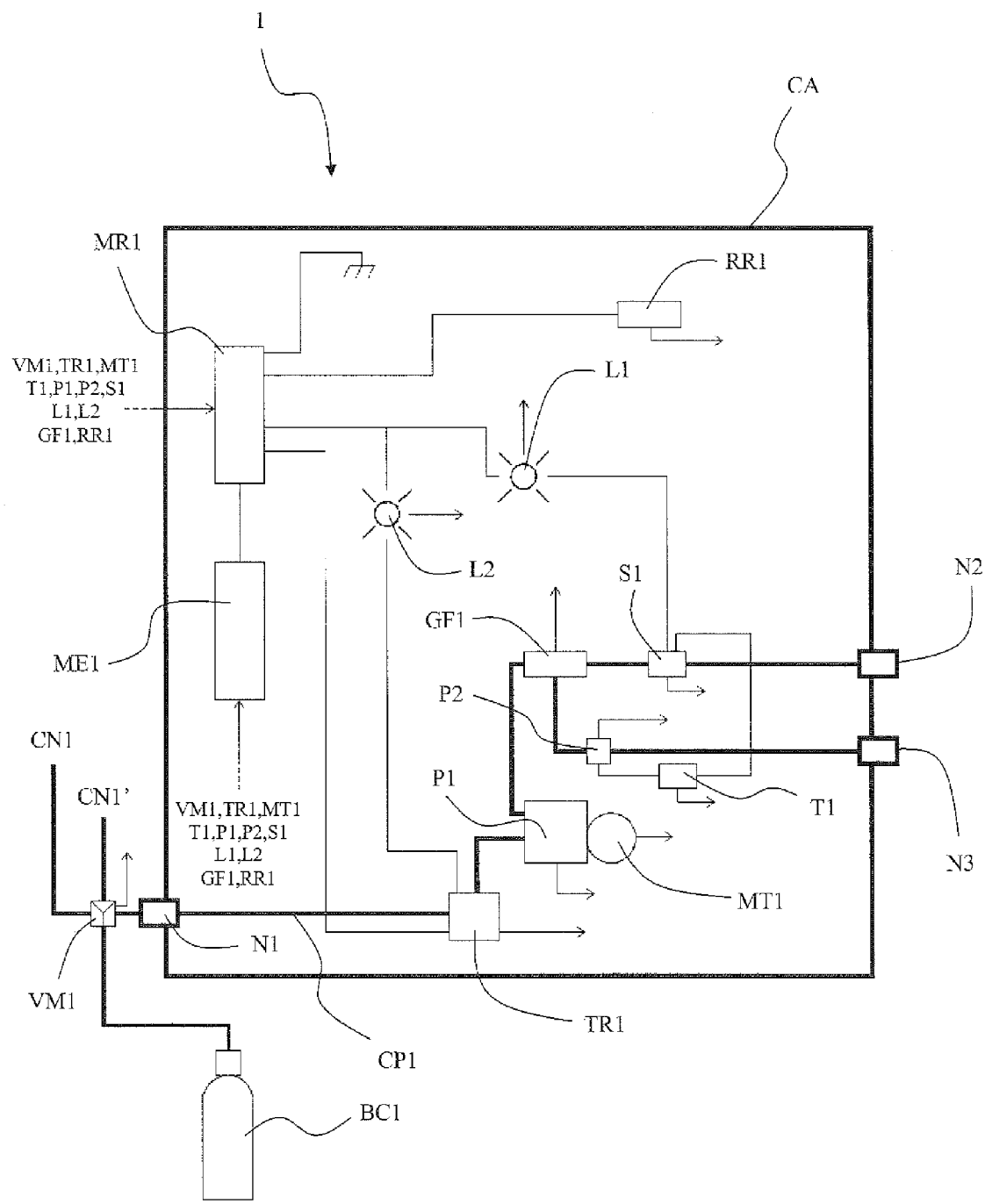
FIG. 1 shows a circuit diagram of the device for analysing the internal atmosphere of the casing of an electric rotating machine according to the invention.

With reference to the annexed figures, reference numeral 1 globally indicates a device for analysing the internal atmosphere of the casing 10 of an electric rotating machine 20 according to the present invention.

In the present description and following claims, electric rotating machines refers to both synchronous and asynchronous machines, preferably electric rotating machines operating in alternating current.

Figure 2:
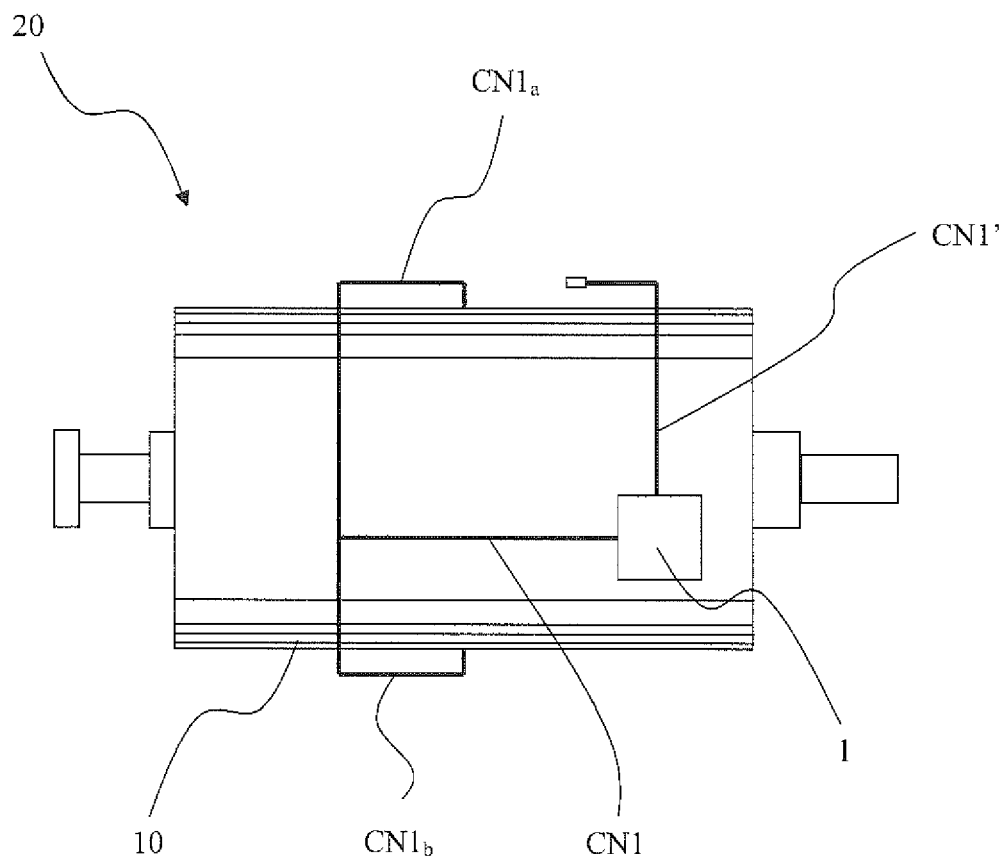
FIG. 2 shows a side view of an electric rotating machine whereto the device of FIG. 1 is associated.

With reference to the example shown in FIG. 2, device 1 is intended to be associated to an electric rotating machine 20 in order to analyse the atmosphere present within casing 10 of the electric rotating machine 20.

To this end, device 1 has a housing CA connectable to casing 10 of the electric rotating machine 20. Preferably, housing CA comprises an explosion-proof box.

In one embodiment, a plurality of inlet/outlet openings is obtained in housing CA. The inlet/outlet openings may be of the receptacle type, preferably threaded, and connectable to various types of conduits.

Device 1 is connected to casing 10 of the electric rotating machine 20 by an atmosphere inlet conduit CN1 adapted to place the interior of said casing 10 in fluid communication with an inlet opening N1 formed in housing CA.

The atmosphere inlet conduit CN1 is connected to the atmosphere inlet opening N1 of housing CA.

Housing CA therein has a suction pump P1 for drawing the atmosphere present within casing 10 of the electric rotating machine 20.

The suction pump P1 is in fluid communication with the atmosphere inlet conduit CN1 through a further pump inlet conduit CP1. In the practice, the suction pump P1 draws the atmosphere present within casing 10 of the electric rotating machine 20 thanks to the fluid circuit created between the atmosphere inlet conduit CN1, the inlet opening N1 and the pump inlet conduit CP1.

Preferably, the pump inlet conduit CP1 is arranged in the housing CA.

In one embodiment, the suction pump P1 is of the air sampling type and actuable by an electric motor MT1 connected thereto.

Device 1 may comprise two or more atmosphere inlet conduits in fluid communication with casing 10 of the electric rotating machine 20.

In a preferred embodiment, it is for example possible to connect a first atmosphere inlet conduit $CN1_a$ at a top portion of casing 10 relative to the rotor of the electric rotating machine 20 and a second atmosphere inlet conduit $CN1_b$ at a bottom portion of casing 10 relative to the rotor of the electric rotating machine 20. In this way, advantageously, it is possible to determine the presence and the value of percentage volume of light gases and/or heavy gases present in the atmosphere to be analysed.

As shown in the example of FIG. 2, the device may comprise valve means (not shown) in fluid communication with the atmosphere inlet conduit CN1 in order to divert the flow from the first atmosphere inlet conduit $CN1_a$ and/or from the second atmosphere inlet conduit $CN1_b$ towards the atmosphere inlet conduit CN1.

According to an embodiment, device 1 is provided with transducer means S1 adapted to measure the percentage volume of at least one explosive compound present in the atmosphere to be analysed and adapted to generate an electric signal proportional to the percentage volume of the explosive compound analysed.

Device 1 also comprises comparison means (not shown) connected to the transducer means and adapted to compare the value of the percentage volume of the explosive compound analysed with a predetermined threshold value of percentage volume (Vs).

The comparison means are adapted to generate an electric alarm signal when said predetermined threshold value (Vs) is exceeded.

According to an embodiment, device 1 comprises switching means (not shown) connected to the electric rotating machine 20 and adapted to receive the electric alarm signal in order to interrupt the supply to the same electric machine 20.

Through the pneumatic connection of device 1 with the interior of casing 10 of the electric rotating machine 20 it is possible to measure the percentage volume of at least one explosive compound present in the atmosphere within casing 10 of the electric rotating machine 20. In the practice, through the suction pump P1 it is possible to send the atmospheric flow to the transducer means S1 in order to analyse the atmosphere within casing 10 of the electric motor 20.

Preferably, the transducer means S1 are arranged in the housing CA.

In one embodiment, the transducer means S1 are arranged outside the housing CA.

To this end, the transducer means S1 may comprise at least one electrochemical cell sensor.

The electrochemical cell is for example intended for determining the percentage value of ammonia $NH_3$ and/or sulphydric acid $H_2S$ present in the internal atmosphere of casing 10 of the electric rotating machine 20. In one embodiment, the electrochemical cell is for example intended for determining the percentage value of hydrogen $H_2$.

In one embodiment, the transducer means S1 may comprise at least one infrared sensor. The infrared sensor is intended, for example, for determining the value of heptane, methane, propane, butane, liquid petroleum gas (LPG), naphtha vapours, kerosene vapours, gas oil vapours, vacuum gas oil (gaseous state), vacuum residue (gas state), methanthiol, distillation residue vapours.

In one embodiment, the transducer means S1 exhibit an electrochemical cell sensor and an infrared sensor connected in a pneumatic series to each other. The serial connection may be configured so that the atmospheric flow intercepts the electrochemical cell sensor first or, alternatively, intercepts the infrared sensor first.

In one embodiment, the transducer means S1 may exhibit two electrochemical cell sensors and one infrared sensor connected in a pneumatic series to each other. The serial connection is configured so that the atmospheric flow intercepts the two electrochemical cell sensors first.

In one embodiment, the serial connection is configured so that the atmospheric flow intercepts an electrochemical cell sensor first, then the infrared sensor and, at the end, the other electrochemical cell sensor. With reference again to the example shown in FIG. 1, an atmosphere outlet opening N2 is obtained in the casing, connected to an atmosphere outlet conduit CN2 in fluid communication with the suction pump P1. In this way, the atmosphere outlet conduit CN2 is intended to eject the atmosphere drawn by pump P1 outside housing CA through the atmosphere outlet opening N2.

It should be noted that the operating conditions of device 1 may vary within a range of temperatures comprised between, for example, −20° C. and +60° C. Condensation may form inside the conduits of device 1 which may distort the measurement of the atmosphere to be analysed. In order to eliminate any condensation, the device may comprise at least one filter GF1 arranged between the suction pump P1 and the transducer means S1 for filtering the condensation present in the fluid path between the suction pump P1 and the transducer means S1. As shown in FIG. 1, a condensation outlet opening N3 is obtained in casing 10, connected to a condensation outlet conduit CN3 in fluid communication with filter GF1.

In order to eject any condensation from the conduits, device 1 is provided with a peristaltic pump P2 connected to filter GF1 and adapted to draw the filtered condensation and eject it through the condensation outlet opening N3.

In one embodiment, the ejection of condensation may be regulated and timed by a condensation discharge timer T1 connected to the peristaltic pump P2.

The peristaltic pump P2 may be actuated by a motor connected thereto (not shown).

In one embodiment, in order to regulate the temperature within housing CA, device 1 is provided with a resistance temperature detector RR1 connectable inside housing CA.

In one embodiment, in order to regulate the temperature of the atmosphere drawn by pump P1 and intended for the transducer means S1, device 1 according to the invention is provided with a resistance temperature detector TR1 associated with the pump inlet conduit CP1.

Preferably, the resistance temperature detector TR1 is arranged between the pump inlet conduit CP1 and the pump P1.

According to an embodiment, device 1 is adapted to analyse the atmosphere directly outside casing 10 of the rotating machine 20. To this end, the device may exhibit a second inlet conduit CN1' in fluid communication with the atmosphere inlet opening N1. For example, the free end of the second inlet conduit CN1' may be arranged on top or underneath casing 10 relative to the rotor of the rotating machine 20 so as to draw the atmosphere outside casing 10 of the same rotating machine 20.

The device 1 comprises valve means VM1 in fluid communication with the atmosphere inlet opening N1 and adapted to intercept the atmosphere flow flowing through the first CN1 and/or the second inlet conduit CN1'. Said valve means VM1 are, for example, of the two-way type and movable between a first position and a second position so that the transducer means S1 alternately receive the atmosphere flow from the first inlet conduit CN1 and/or from the second inlet conduit CN1'. In this way, the transducer means S1 may measure the percentage volume of an explosive compound optionally present, alternatively, in the atmosphere within casing 10 or in the atmosphere directly outside casing 10 of the electric rotating machine 20.

In one embodiment, the valve means VM1 are adapted to directly draw the atmosphere outside casing 10 of the rotating machine 20.

With reference to the transducer means. S1, it should be noted that the electrochemical cell sensors and/or the infrared sensors need to be calibrated to a predetermined threshold value of percentage volume (or parts per million).

Advantageously, each sensor is calibrated with respect to a compound to which it is less sensitive. In this way it is possible to determine all the potentially explosive compounds (or mixtures of explosive compounds) based on the lower explosive limits LEL set by the regulations or according to the usage requirements of device 1.

By way of an example, below is a list of the results of some tests run for calibrating the transducer means S1.

With reference to an electrochemical cell sensor, it was calibrated with ammonia $NH3_3$ to a threshold level Vs of 800 ppm. In this way, the following compounds were determined:
ammonia: Vs=0.5% (LEL),
sulphydric acid: Vs<6% (LEL).

In another test, an electrochemical cell sensor was calibrated with carbon dioxide to a threshold level Vs of 800 ppm. Accordingly, the following compounds were determined:
hydrogen: Vs<5% (LEL).

In a further test, an infrared sensor was calibrated with heptane $CH_3$ $(CH_2)5CH_3$ to a threshold level Vs considered at 30% of the lower explosive limit LEL. In this way, the following compounds were determined:
Heptane: Vs=30% (LEL),
Methane: Vs=19% (LEL),
Ethane: Vs<23% (LEL),
Propane: Vs=23% (LEL), Butane: Vs=25% (LEL),
Liquid petroleum gas (LPG): Vs=25% (LEL),
Fuel gas: Vs=25% (LEL),
Naphtha vapours: Vs<25% (LEL),
Kerosene vapours: Vs<28% (LEL),
Gas oil vapours: Vs<28% (LEL),
Vacuum gas oil (gas state): Vs<28% (LEL),
Vacuum residue (gas state): Vs<25% (LEL),
Methanthiol: Vs<20% (LEL),
distillation residue vapours: Vs<20% (LEL).

In order to calibrate the transducer means S1, device 1 according to the invention may be connected to a calibration tank BN1 adapted to emit at least one compound for calibrating the transducer means 1 and in fluid communication with the valve means VM1. For example, according to the calibration requirements it is possible to use one or more tanks BN1 (for example a cylinder) each containing one of the compounds listed above in order to send it to the transducer means S1 for the calibration thereof.

In one embodiment, the valve means VM1 are of the three-way type and movable between three positions so as to intercept the atmosphere flow alternately coming from the first inlet conduit CN1, from the second inlet conduit CN1' or from the calibration tank BN1.

In one further embodiment, the valve means VM1 may be arranged inside the housing CA. This embodiment allows, for example, to provide of dedicated inlet apertures (not shown) formed in the housing CA for the first inlet conduit CN1, the second inlet conduit CN1' and the calibration tank BN1.

In one embodiment, device 1 comprises a numeric keypad connected with the transducer means for setting a desired threshold value of percentage volume Vs. In this way it is possible to set the threshold values Vs of the sensors based on the usage requirements of device 1.

In one embodiment, device 1 comprises first lighting means L1 in signal communication with the transducer means S1 and adapted to emit light signals based on the electric alarm signal generated. In particular, the first lighting means L1 emit a light signal if device 1 determines a higher atmosphere explosive level than a predetermined threshold value of percentage volume.

In one embodiment, device 1 comprises second lighting means L2 in signal communication with the resistance temperature detector TR1 or the resistance temperature detector RR1 and intended for emitting light signals based on the temperature level measured within housing CA. To this end, one or more temperature sensors may be provided, connectable to the device conduits or to the housing for determining the operating temperature of device 1.

The device may comprise different visual means such as displays, screens, etc. in order to emit visual signals informing about an explosive alarm condition or the operating temperature of device 1.

In one embodiment, device 1 comprises power supply means MR1 for supplying the following components housed within device 1: suction pump P1, electric motor MT1, peristaltic pump P2, transducer means S1, filter GF1, valve means VM1, resistance temperature detectors TR1, RR1, lighting means L2, L3.

As shown in the example of FIG. 1, device 1 also comprises processing means ME1 for controlling the activation/deactivation of suction pump P1, peristaltic pump P2, transducer means S1, filter GF1, valve means VM1, resistance temperature detectors TR1, RR1 and/or lighting means L2, L3 based for example on appropriate programming executed by PLC or dedicated processors.

In one embodiment, the processing means ME1 are supplied by the power supply means MR1.

As it can be understood from the description, the device for analysing the internal atmosphere of the casing of an electric rotating machine according to the present invention allows meeting the needs and overcoming the drawbacks mentioned in the introductory part of the present description with reference to the prior art.

Of course, a man skilled in the art may make several changes and variations to the device according to the invention described above in order to meet specific and incidental needs, all falling within the scope of protection defined in the following claims.

The invention claimed is:

1. An electric rotary machine placed in a casing and associated with a device for analyzing the atmosphere inside and directly outside the case of said rotary electric machine, said device comprising:
    a housing with an atmosphere inlet opening, said housing being connectable to said casing of said electric rotary machine,
    a suction pump for sucking in the atmosphere inside said case of said electric machine,
    a pump inlet duct to place said atmosphere inlet opening in fluid communication with said suction pump,
    a first atmosphere inlet duct suitable for placing inside of said case in fluid communication with said atmosphere inlet opening,
    a second atmosphere inlet duct suitable for placing directly outside of said case in fluid communication with said inlet opening,
    a transducer structured and arranged to measure the percentage volume of at least one explosive compound present in said atmosphere sucked in by said pump and to compare said percentage volume of at least one explosive compound with a predetermined threshold percentage volume value, said transducer generating an electric signal proportional to the percentage volume of said at least one explosive compound and generating an alarm signal once said predetermined threshold value has been exceeded,
    at least one filter arranged between said pump and said transducer for filtering the condensation present in the fluid path between said suction pump and said transducer,
    a resistance temperature detector associated with said pump inlet duct and suitable for adjusting the temperature of said internal atmosphere sucked in by said suction pump, wherein:
    said suction pump and said pump inlet duct are arranged in said housing, and
    wherein said device comprises a valve in fluid communication with the atmosphere inlet opening structured and arranged to intercept the atmosphere flow flowing through the first atmosphere inlet duct and/or the second atmosphere inlet duct.

2. The electric rotary machine according to claim 1, wherein the device comprises:
    a condensate outlet opening arranged in said housing,
    a condensate outlet duct in fluid communication with said at least one filter and said condensate outlet opening,
    a peristaltic pump suitable for sucking in the filtered condensation from said at least one filter and expelling it outside of said housing from said condensate outlet opening.

3. The electric rotary machine according to claim 1, wherein the device comprises:

an atmosphere outlet opening formed in said housing, an atmosphere outlet duct in fluid communication with said suction pump and intended to expel said sucked in atmosphere outside of said housing from said atmosphere outlet duct.

4. The electric rotary machine according to claim 1, wherein said transducer means of the device is arranged in said housing.

5. The electric rotary machine according to claim 1, wherein said transducer means of the device is arranged outside said housing.

6. The electric rotary machine according to claim 1, wherein said valve means are of the two way type and movable between a first position and a second position so that the transducer alternately receives the atmosphere flow from the first atmosphere inlet duct and/or the second atmosphere inlet duct.

7. The electric rotary machine according to claim 1, wherein said transducer of the device comprise:
   at least one electrochemical cell sensor,
   at least one infrared sensor.

8. The electric rotary machine according to claim 7, wherein said at least one electrochemical cell sensor and said at least one infrared sensor of the device are suitable for measuring the percentage volume of at least one from hydrogen, hydrogen sulphide, ammonia, methane, ethane, propane, butane, liquefied petroleum gas (LPG), naphtha vapour, kerosene vapour, diesel fuel vapour, vacuum gas oil (aeriform state), de-asphalted oils (aeriform state) and mercaptans and their mixtures.

9. The electric rotary machine according to claim 7, wherein said at least one electrochemical cell sensor and said at least one infrared sensor of the device are connected pneumatically in series with each other.

* * * * *